United States Patent [19]

van der Jagt

[11] Patent Number: Plant 6,090

[45] Date of Patent: Jan. 26, 1988

[54] CHRYSANTHEMUM NAMED "BLUE REFLA"

[75] Inventor: Martinus van der Jagt, Ter Aar, Netherlands

[73] Assignee: Chrysanthemum Breeders Association N.V., Netherlands Antilles

[21] Appl. No.: 775,407

[22] Filed: Sep. 12, 1985

[30] Foreign Application Priority Data

Sep. 14, 1984 [NL] Netherlands ..... CHR 928

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Parkhurst & Oliff

[57] ABSTRACT

A new and distinct cultivar of Chrysanthemum plant named "Blue Refla", bearing medium sized blooms with a rose color.

5 Drawing Figures

BACKGROUND OF THE INVENTION

The present invention comprises a new and distinct cultivar of Chrysanthemum plant which is a cross of unknown parents. The invention was discovered by Martinus van der Jagt in September, 1983 at Paradijsweg 88, Ter Aar, Holland. The invention has been asexually reproduced by cuttings at the same location. The new cultivar has been found to retain its distinctive characteristics through successive propagations.

SUMMARY OF THE INVENTION

The present invention is a new and distinct variety of Chrysanthemum of medium sized blooms and rose color.

BRIEF DESCRIPTION OF THE DRAWINGS

The present invention of a new and distinct variety of Chrysanthemum is shown in the accompanying drawings, the color being as nearly true as possible with color photographs of this type.

FIG. 1 shows the full bloom of the new cultivar.

FIG. 2 shows various stages of bloom of the new cultivar.

FIG. 3 shows the foliage and stem of the new cultivar.

FIG. 4 shows another view of the full bloom of the cultivar.

FIG. 5 shows a reverse view of FIG. 3 of the foliage and stem of the new cultivar.

DESCRIPTION OF THE INVENTION

This new variety of Chrysanthemum is of the botanical classification *Chrysanthemum morifolium* named Blue Rafla. When grown in the vicinity of Ter Aar, Holland, it has a response time of approximately 8½ weeks. This new variety produces medium sized blooms of rose color and having a green yellow center with an 18 day performance. This new variety of Chrysanthemum has been found to retain its distinctive characteristics throughout successive propagations and may be planted under greenhouse conditions in Holland between weeks 1-36.

The following is a description of the plant and characteristics that distinguish it over related known varieties and antecedents:

Bud:
- *Size.*—Medium.
- *Form.*—Flat top.
- *Color.*—Bishops violet R.H.S. 34/2.

Botanical classification: *Chrysanthemum morifolium.*

Bloom:
- *Size.*—Medium.
- *Fully open.*—7 cms.
- *Borne.*—Singly.
- *Stems.*—Strong.
- *Form.*—Single.
- *Permanence.*—18 days.

Color:
- *Center of flower.*—Sap green R.H.S. 62.
- *Base of petals.*—Neyron Rose, R.H.S. 623/2.
- *Inside of petals.*—Neyron Rose, R.H.S. 623/2.
- *Reverse of petals.*—Neyron Rose, R.H.S. 623/2.
- *Outer petals.*—Neyron Rose, R.H.S. 623/2.
- *Tonality from a distance.*—Dark pink single.
- *Discoloration.*—None.

Petals:
- *Texture.*—Rough (both upper and underside).
- *Number.*—33-37.
- *Arrangement.*—Imbricated.
- *Persistence.*—Petals strong. Some reflexion at edge when over bloomed.
- *Fragrance.*—Typical Chrysanthemum.

Reproductive organs:
- *Stamens.*—Normal for single.
- *Pollen.*—Some appears when blooming.
- *Styles.*—Columnar.
- *Length.*—Medium.
- *Stigmas.*—Normal yellow.
- *Ovaries.*—Enclosed in calyx.

Plant:
- *Form.*—Herbaceous.
- *Growth.*—Vigorous.
- *Height.*—Tall.
- *Peduncle.*—Strong.

Foliage:
- *Color.*—Normal to dark green.
- *Size.*—Medium.
- *Quantity.*—Normal to less.
- *Shape.*—Pointed.
- *Texture.*—Upper and underside smooth.
- *Veins.*—Normal.
- *Edge.*—Deeply undulated.

*Leaf underside.*—Smooth.
*Leaf upperside.*—Rough.

In the description above, color referfences are made to The Horticultural Colour Chart I & II issued by The British Colour Council in collaboration with The Royal Horticultural Society, Copyright Robert F. Wilson, Vol I, 1938; Vol II, 1941, printed by Henry Stone & Son, Ltd., Banbury, England.

I claim:

1. A new and distinctive variety of Chrysanthemum named Blue Rafla as described and illustrated in the foregoing specification and accompanying drawings.

* * * * *

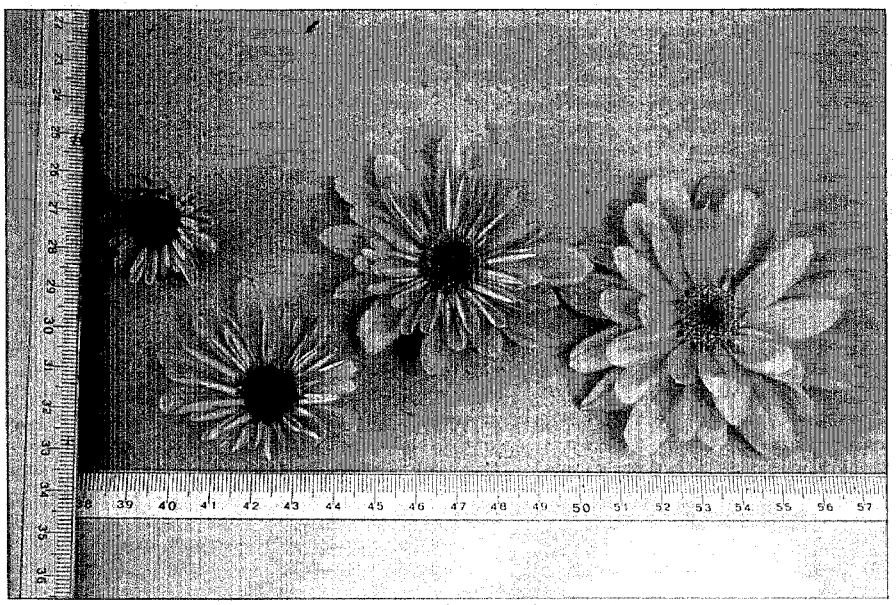

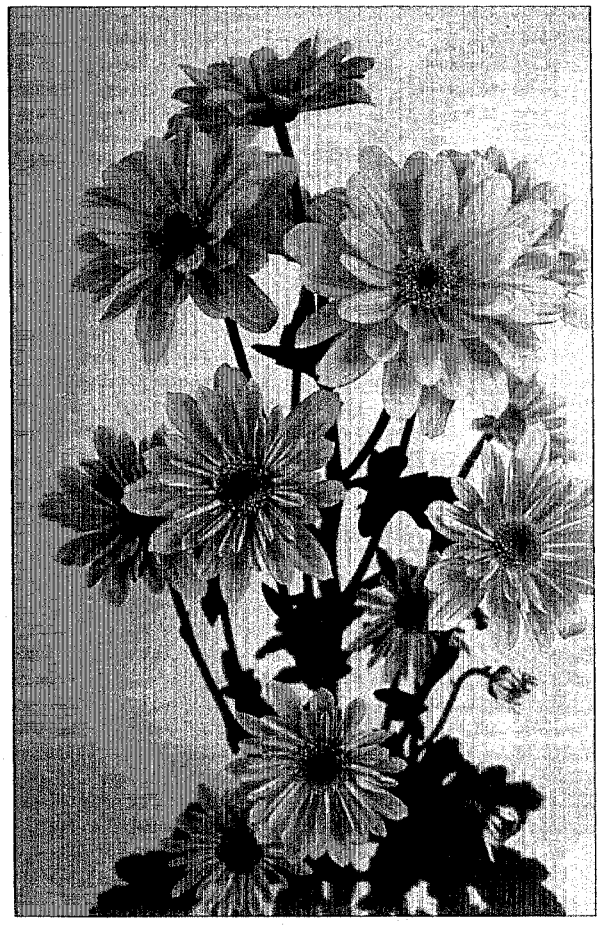

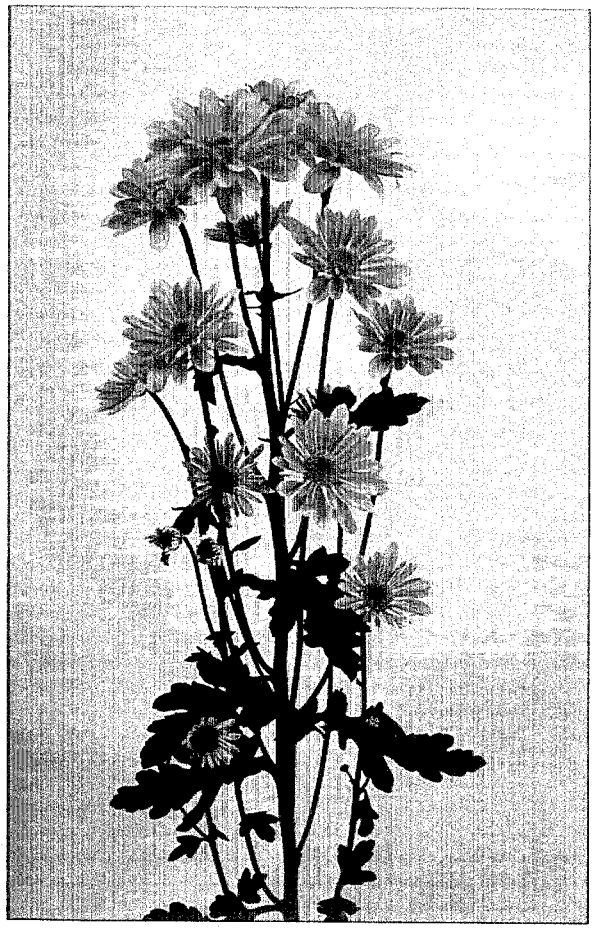

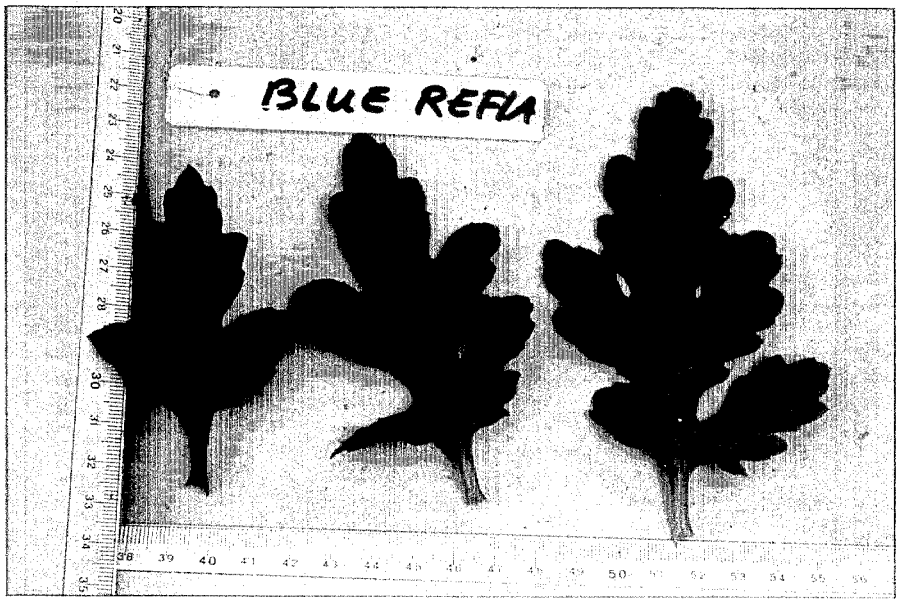
BLUE REFLA

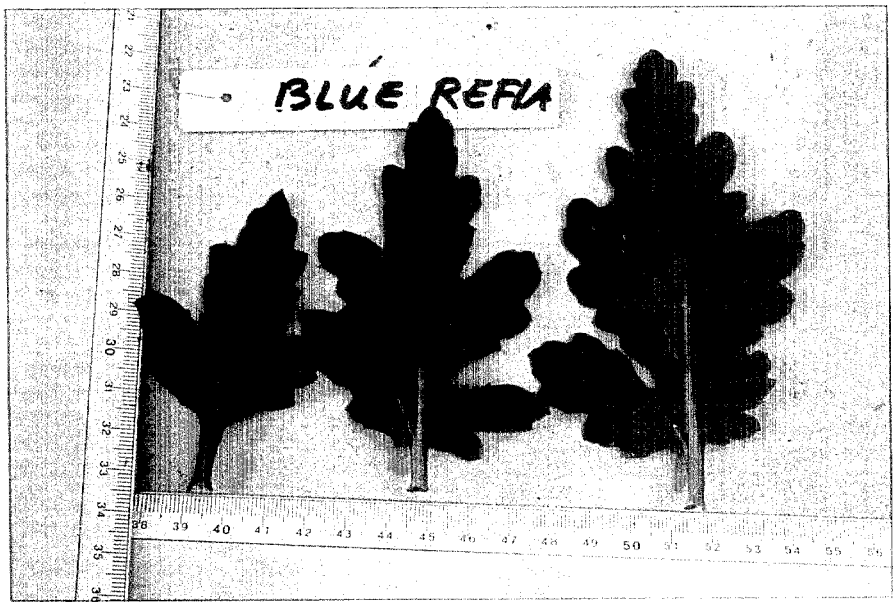
BLUE REFIA